United States Patent [19]
Dusek

[11] Patent Number: 5,693,057
[45] Date of Patent: Dec. 2, 1997

[54] INSTRUMENT FOR IMPLANTING FOLDABLE INTRAOCULAR LENSES

[76] Inventor: Vaclav Dusek, 6210 Lake Washington Bvd. SE., Bellevue, Wash. 98006

[21] Appl. No.: 549,011

[22] Filed: Oct. 27, 1995

[51] Int. Cl.⁶ .................................................. A61F 09/00
[52] U.S. Cl. ................... 606/107; 606/205; 606/206; 606/210
[58] Field of Search .................... 606/107, 205, 606/206, 207, 210; 623/6

[56] References Cited

U.S. PATENT DOCUMENTS

| | | | |
|---|---|---|---|
| 3,906,957 | 9/1975 | Weston | 606/210 |
| 4,759,359 | 7/1988 | Willis et al. | 606/107 |
| 4,873,979 | 10/1989 | Hanna | 606/210 |
| 5,007,913 | 4/1991 | Kulebohn et al. | 606/107 |
| 5,100,410 | 3/1992 | Dulebohn | 606/107 |
| 5,176,686 | 1/1993 | Poley . | |
| 5,176,701 | 1/1993 | Dusek et al. . | |
| 5,178,622 | 1/1993 | Lehner, II | 606/107 |
| 5,190,553 | 3/1993 | Kanert et al. . | |
| 5,217,464 | 6/1993 | McDonald . | |
| 5,222,972 | 6/1993 | Hill et al. . | |
| 5,275,604 | 1/1994 | Rheinish et al. . | |
| 5,290,293 | 3/1994 | Van Noy et al. . | |
| 5,304,182 | 4/1994 | Rheinish et al. . | |
| 5,334,215 | 8/1994 | Chen | 606/210 |
| 5,354,333 | 10/1994 | Kammann et al. . | |

FOREIGN PATENT DOCUMENTS 1697796 12/1991 U.S.S.R. ................ 606/210

OTHER PUBLICATIONS

Rhein Medical, Th Fine Universal II Forceps & Fine Holder, pp. 1–3 1995.
Alcon Laboratories, Inc., "Folding System & Implantation Guide", 4 pp., publication date unknown.
Rhein Medical, Inc., "The Fine* Universal II Forceps & Fine* Holder™", Advertisement, publication date unknown.
Rhein Medical, Inc., "The Lindstrom* Folder™", Advertisement, publication date unknown.

*Primary Examiner*—Robert A. Hafer
*Assistant Examiner*—Justine R. Yu
*Attorney, Agent, or Firm*—Christensen O'Connor Johnson & Kindness

[57] ABSTRACT

Two elongated side plates are pivotally connected together for rotation about an axis extending lengthwise of and between the side plates. Thin, elongated necks extend distally from the side plates to a pair of jaws configured to grasp and release a foldable intraocular lens. The necks connecting the jaws to the side plates are shaped such that adjacent points are substantially intersected by the axis, with such intersection point located to be positioned at approximately the corneal incision during a lens implantation procedure. Thus, with the jaws positioned interiorly of the lens capsule, the jaws can be swung between open and closed positions without unnecessary stretching of the corneal incision.

12 Claims, 3 Drawing Sheets

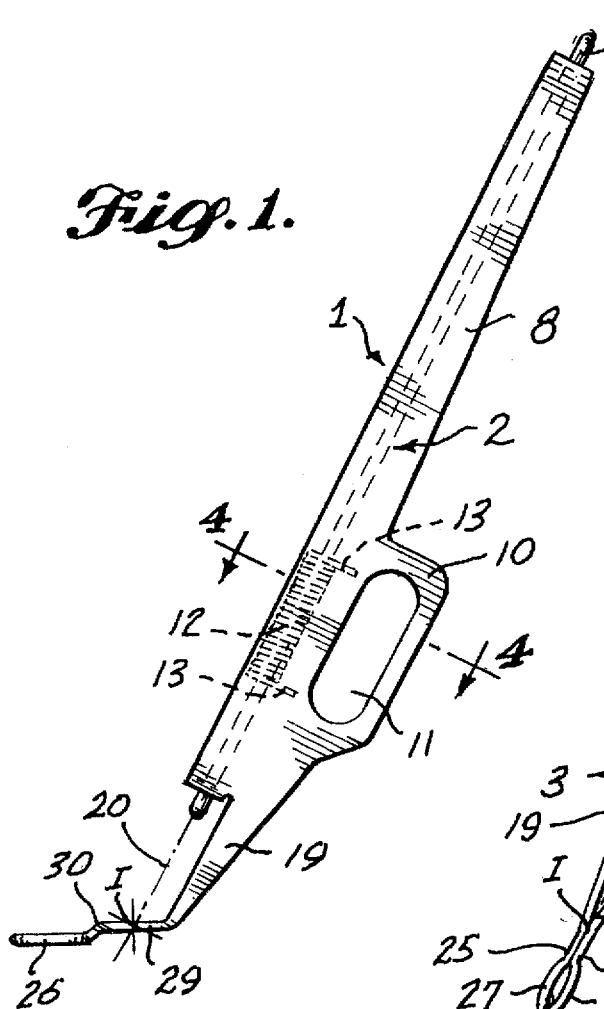
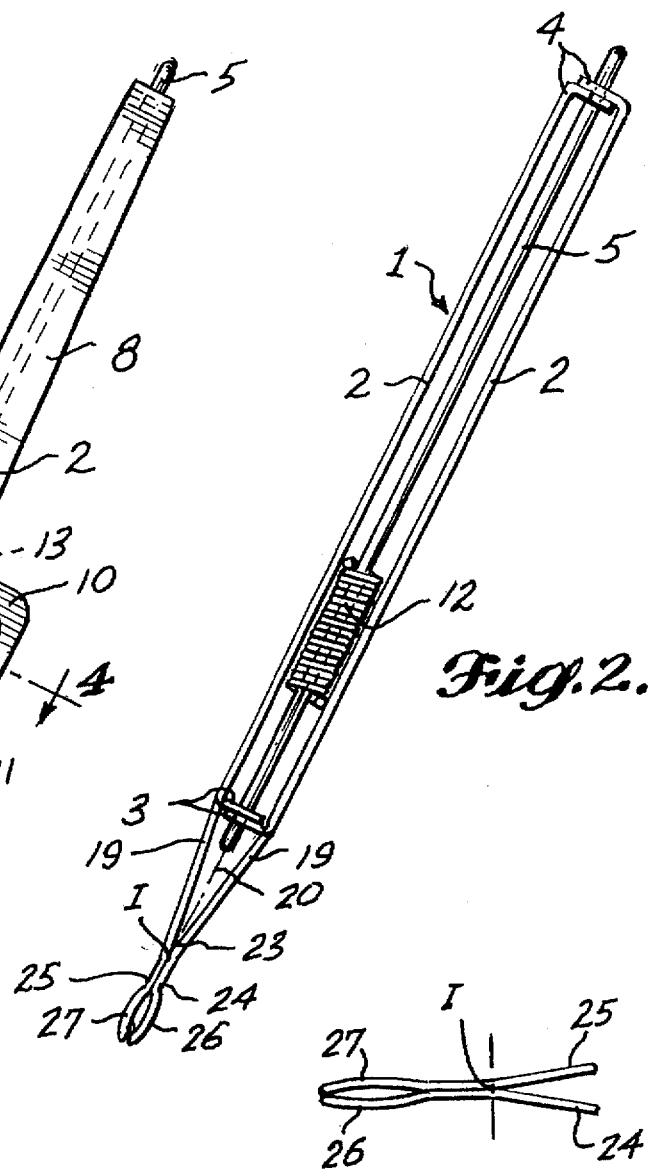
Fig. 1.
Fig. 2.
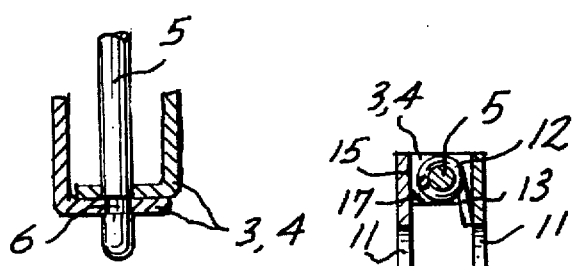
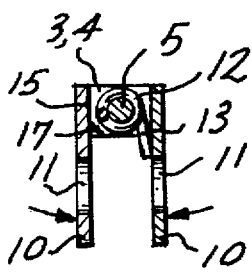
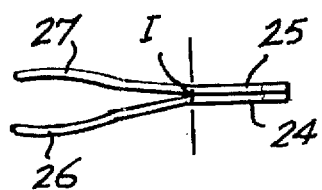
Fig. 3.
Fig. 4.
Fig. 5.
Fig. 6.

INSTRUMENT FOR IMPLANTING FOLDABLE INTRAOCULAR LENSES

FIELD OF THE INVENTION

The present invention relates to the general field of surgical instruments, and more specifically to a forceps-type instrument used during cataract surgery for insertion of an artificial lens in an otherwise natural eye.

BACKGROUND OF THE INVENTION

Moving from the exterior toward the center, a human eye includes the cornea, anterior chamber behind the cornea, iris, posterior chamber behind the iris, and vitreous body which encompasses the major portion of the volume of the eyeball. The lens is located in the posterior chamber behind the iris and in front of the vitreous body, and consists of a relatively hard central nucleus surrounded by the softer cortex enclosed in a membrane called the capsule. The capsule and the lens structure are held in position centered behind the iris by fibers called zonules that extend between the lens capsule and the periphery of the posterior chamber.

In modern cataract surgery, an incision is made along the margin of the cornea for access to the lens through the central opening of the iris (pupil). The lens capsule is opened adjacent to the iris and the cloudy natural lens is removed. Preferably, the posterior portion of the lens capsule is left intact so that the posterior chamber remains isolated from the vitreous. Also, the zonules are not disturbed so that the opened lens capsule continues to be supported in the posterior chamber.

In a popular form of cataract surgery, an artificial intraocular lens is implanted after the natural lens has been removed. The intraocular lens includes a clear central optical portion to replace the clear natural lens of an undamaged and undiseased eye. The intraocular lens is designed to be centered in the posterior chamber. In a common form of intraocular lens, two thin, flexible but slightly resilient filaments called haptics are spiralled tangentially outward from opposite sides of the optical portion of the intraocular lens. The entire artificial lens structure is preferably implanted in the natural lens capsule. The haptics engage against the inner periphery of the capsule and, like weak leaf springs, gently support the optical portion of the artificial lens centered behind the iris.

Typically, the artificial lens is of a diameter of about six millimeters, necessitating a corneal incision of greater than that length in order to accommodate the lens and the inserted portion of the grasping or forceps instrument. In order to allow for smaller incisions, thereby reducing the trauma to the eye, lenses which are formed of soft material foldable about a diameter have been developed, along with associated instruments for folding the soft lenses and for grasping and inserting them. Ideally, the length of the corneal incision can be approximately one-half the length required if an unfolded lens is used.

It should be understood that the grasping end portions or jaws of the forceps instrument must reliably hold the soft lens in its folded condition, and must be capable of being opened for releasing the folded lens into the lens capsule. Also, precise positioning of the lens is required because any misalignment during insertion or adjustment of the position of the lens or a haptic requires movement of the distal portion of the forceps extending through the corneal incision. Since the incision is made as small as possible, such movement, or simply the bulk of the instrument itself, can stretch and tear the incision, which can be even less desirable than making a longer incision to begin with.

SUMMARY OF THE INVENTION

The present invention provides a forceps instrument having small elongated jaws for grasping and releasing a foldable intraocular lens. Thin, elongated necks extend proximally from the jaws to the body of the instrument which includes larger integral side plates. In profile, the length of each side plate extends at an angle to the associated neck and jaw. The two side plates are pivotally connected together for rotation about an axis extending lengthwise of the side plates. The location of the axis is selected to pass between adjacent surfaces of the necks at a point intermediate their opposite ends, i.e., intermediate the points of connection of the necks to the jaws and the side plates, respectively. Preferably, the necks are designed such that their adjacent surfaces engage at the point of intersection with the swinging axis. Such point is located approximately midway between the opposite ends of the necks.

From the intersection point of the swinging axis with the necks, the two necks diverge either proximally or distally depending on whether the jaws are closed or open. With the jaws closed for gasping an intraocular lens to be implanted, preferably the distal portions of the necks are substantially contiguously engaged. This allows the lens to be inserted through a small corneal incision without stretching the incision by engagement of the jaws or their necks. The length of the necks is selected such that the intersection point is located approximately at the corneal incision (the sizes of adult eyeballs vary very little such that the point at which the instrument passes through the corneal can be estimated very closely).

To release the lens into the capsule, the jaws can be swung to an open position where the distal portions of the necks diverge from the intersection point toward the jaws, but move closer together, preferably into contiguous engagement, proximally from the intersection point toward the body of the instrument. In effect, the jaws rotate about the intersection point which is located at the corneal incision, such that minimal spreading of the jaws in this area occurs during implantation of the lens. Moreover, the interconnection defining the axis of rotation is remote from the jaws, back in the area where side plates are joined together, such that the jaws and necks can be thin and narrow with no bulky pivot pins or other connecting or crossing structure. Rather, the jaws simply lie side by side, which results in a compact arrangement during implantation of the lens. After the lens is released, the jaws are closed again for removal back through the incision without stretching it.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a side elevation of an instrument for implanting foldable intraocular lenses in accordance with the present invention;

FIG. 2 is a top plan of the instrument of FIG. 1;

FIG. 3 is a fragmentary enlarged longitudinal section of an end portion of the body of the instrument of FIG. 1;

FIG. 4 is a transverse section along line 4—4 of FIG. 1;

FIG. 5 is a fragmentary plan of the distal end portion of the instrument of FIG. 1;

FIG. 6 is a fragmentary plan corresponding to FIG. 5 but with parts in different positions;

DETAILED DESCRIPTION OF THE PREFERRED EMBODIMENT

Figure 7:
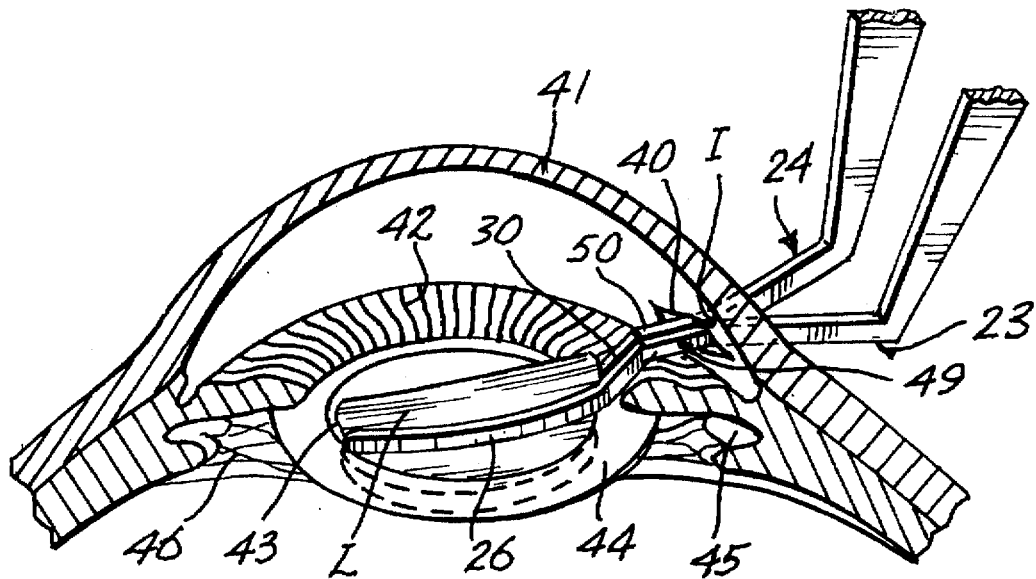
FIG. 7 is an enlarged perspective illustrating use of the instrument of FIGS. 1 through 6 for implanting an intraocular lens, with parts of an eye shown in section.

The instrument of the present invention is used for implanting an intraocular lens, particularly a folded intraocular lens, during cataract surgery. With reference to FIG. 1 and FIG. 2, the preferred instrument 1 includes a graspable body having two elongated side plates 2. As seen in FIG. 2, the opposite ends of the side plates 2 are bent perpendicularly inward, forming overlapping end tabs 3 at the distal end of the body and overlapping tabs 4 at the proximal end of the body. A long and straight pivot shaft 5 extends between the side plates, having its opposite end portions journalled in registered holes in the tabs 3 and 4. As seen in FIG. 3, each end portion of the shaft can have a shallow side notch or circumferential groove 6 for retaining one tab in the position illustrated without interfering with rotation of the side plates relative to each other about the axis of the shaft. The shaft can be forced through the registered tab holes until the groove(s) 6 receive the associated tabs.

As seen in FIG. 1, each side plate has a lateral projection 10 aligned with the projection of the other side plate. Such projections can have knurled outer surfaces or an elongated recess or hole 11 for ease in grasping the instrument between the thumb and forefinger. The trailing portion 8 of the body of the instrument extending proximally from the lateral projections 10 rests between the thumb and forefinger, along the side of the hand, in the approximate position of a pen or pencil held in the hand.

As seen in FIG. 2, a spiral spring 12 has a helical central portion inserted over the shaft 5 in the area of the lateral projections 10. The opposite end portions 13 (FIG. 1) of the spring engage against the inner surfaces of the lateral projections for biasing them apart to the position illustrated in FIG. 2, FIG. 4 and FIG. 5. In such position the flat outer edge 15 (FIG. 4) inner of an tab 3 or 4 of one side plate is engaged against the inner surface of the opposite side plate to act as a stop limiting relative rotation of the side plates in a direction tending to spread the lateral projections 10 apart. However, the corners 17 of the tabs are rounded such that the side plates can be rotated relative to each other in a direction tending to move the lateral projections together, such movement being limited by the outer end portions of such projections coming together.

Proceeding distally along the body of the instrument, the side plates have elongated arms 19 offset from the axis 20 of the shaft 5 in a direction toward the lateral projections 10. Such arms taper in width as seen in FIG. 1 and converge, as best seen in FIG. 2.

The distal ends 23 of the arms are located close together and are joined to side by side necks 24 and 25 that extend to jaws 26 and 27. The jaws and necks are designed for insertion through a corneal incision during implantation of an intraocular lens. Therefore, the necks and jaws are necessarily of extremely small cross section. In the preferred embodiment, the entire instrument is made out of stainless steel, the jaws and necks resembling shafts of rectangular cross section approximately 0.020" high by 0.015" thick. As seen in FIG. 1, the necks extend at an angle of about 50° to the longitudinal axis 20 of the pivot shaft 5, with such axis extending between the neck portions at a point I approximately midway between their opposite ends (referred to herein as the "intersection point"). In the preferred embodiment, the neck portions are about 6.5 millimeters long.

The grasping jaws 26 and 27 can be about 6 millimeters long, i.e., approximately equal to the diameter of a foldable intraocular lens. The proximate ends of the grasping portions of the jaws are integrally joined to the distal ends of the necks by a short inclined step 30. Thus, the jaws extend approximately parallel to the necks, but are offset slightly distally from them.

The side plates 2 of the instrument are biased by the spiral spring to a position in which the side plate projections 10 are spread apart, and the jaws are biased together ("closed"). The relative positions of the jaws in the closed position are shown in FIG. 5. The grasping end portions of the jaws 26, 27 preferably are slightly bowed to accommodate a folded optic of the lens. The necks are straight from the step 30 to the intersection point I and, preferably, substantially contiguously engaged or at least essentially parallel and close together. From the intersection point, the neck portions diverge proximally at a small acute angle, preferably about 18° to 23° relative to each other, to the distal ends of the arms. Squeezing the side plates projections 10 together swings the grasping portions of the jaws apart to the open position shown in FIG. 6. In such position, the jaws are angularly spaced apart, the distal portions of the necks converge proximally to the intersection point, and the proximate portions of the necks are substantially contiguously engaged or at least substantially parallel and close together.

Since the swinging axis 20 of the instrument intersects the necks 24, 25 at approximately the angular midpoint or crook between their proximate and distal portions, there is essentially no relative lateral movement of the necks in that area. Such intersection point is positioned to be approximately aligned with the corneal incision during implantation of the intraocular lens so as to reduce any tendency of the instrument to stretch or tear the incision during implantation and normal adjustment of the position of the lens in the capsule.

Figure 8:
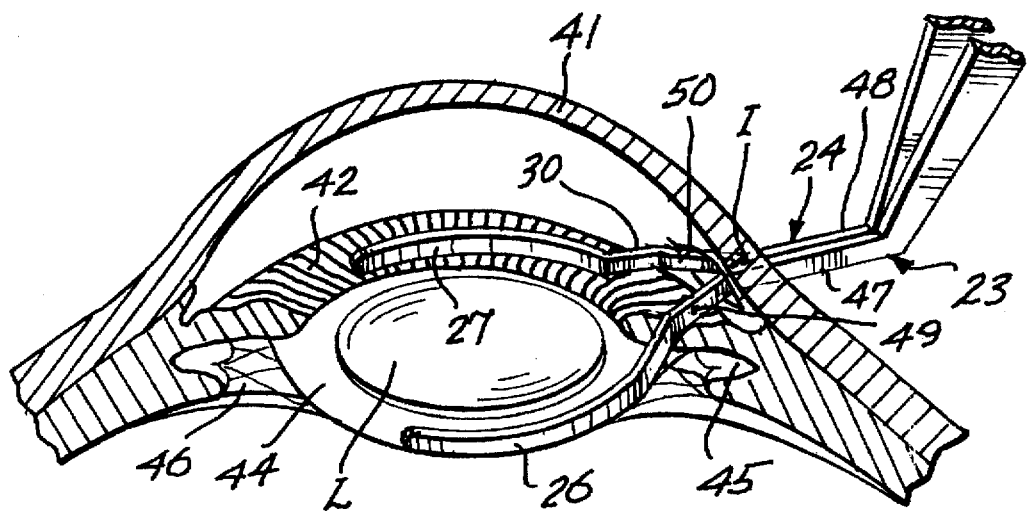
FIG. 8 is an enlarged perspective corresponding to FIG. 7 but with parts in different positions.

More specifically, FIG. 7 and 8 illustrate the approximate positioning of the instrument during lens implantation. Preferably a soft foldable lens L is used, which can be folded by use of any off a variety of conventional folding instruments, followed by grasping of the folded lens between the jaws 26, 27 of the instrument in accordance with the present invention. With the jaws closed and grasping the folded lens, the grasped lens can be inserted through the small incision 40 through the cornea 41, through the aperture of the iris 42, and into the opening 43 of the capsule 44 which has been carefully cut to minimize the trauma to the posterior chamber 45 and supporting fibrous zonules 46. The intersection point I of the necks is positioned at the location of the corneal incision, in the range of 9 millimeters to 9.5 millimeters from the free ends of the jaws, assuming that the jaw is approximately 6 millimeters long so as to span substantially the entire diameter of the lens, or preferably about 6 millimeters to 6.5 millimeters from the center of the lens to the intersection point. The preferred offset achieved by the step 30 is 1 millimeter.

When the lens is released by opening the jaws (FIG. 8), the proximate portions 47, 48 of the necks 23, 24 come together, and the distal portions 49, 50 of the necks spread apart. However, since rotation is about the intersection point I positioned at the corneal incision, there is very little relative movement of the jaws in this area so that the integrity of the incision is not compromised.

In addition, the inclined step 30 between the grasping jaws and the necks allows for convenient insertion Of the lens into the capsule, minimizing manipulation of the instrument which may tend to apply undue pressure at the incision area.

After insertion and release of the lens into the capsule, the jaws are again brought together by releasing the grasp on the lateral projections of the instrument for withdrawal of the closed jaws back through the incision.

Figure 9:
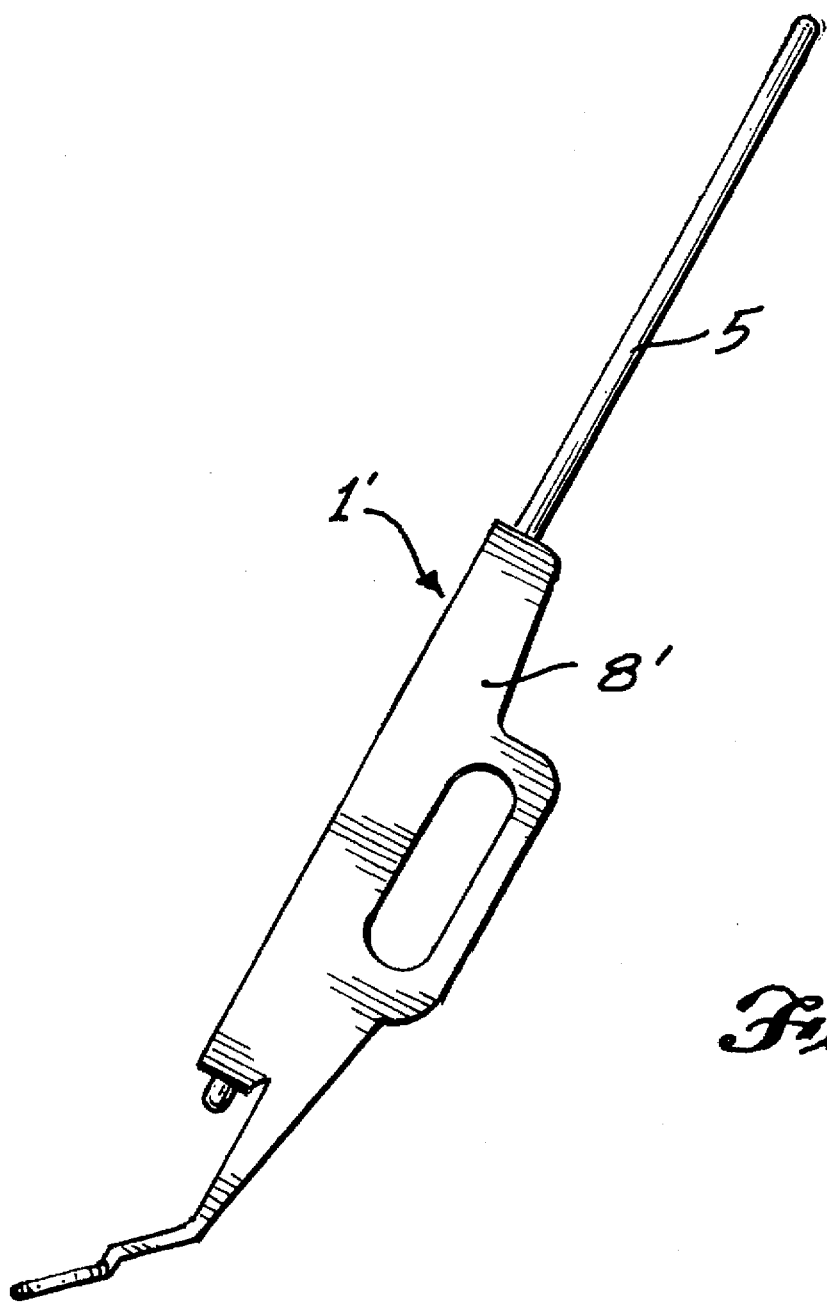
FIG. 9 is a side elevation of an alternative embodiment of an instrument for implanting foldable intraocular lenses in accordance with the present invention.

The embodiment shown in FIG. 9 is identical to the embodiment previously described, except that the proximate portion 8' of the body of the instrument 1' has been shortened. The pivot shaft 5 is of the same length as the embodiment previously described, approximately twice the length of the body of the instrument between its end tabs, for resting in the hand like a pen or pencil. The advantage of the embodiment of FIG. 9 is that the weight of the instrument is reduced, thereby making it easier to manipulate and hold in a desired position. Otherwise, the embodiment of FIG. 9 is identical to the previously described embodiment.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An instrument for implanting an intraocular lens into a lens capsule, through a corneal slit of an eye, comprising two side-by-side jaws adapted to grasp and release the lens, two elongated necks joined, respectively, to the jaws and extending proximally therefrom in uncorrected and uncrossed side-by-side relationship, and a body having relatively swingable portions supporting the necks and jaws for swinging about an axis between a lens grasping position in which the jaws are close together and a lens releasing position in which the jaws are farther apart, the necks having respective adjacent portions defining an intersection point adapted to be located at the corneal incision when the lens is held in the capsule by the jaws and the axis substantially intersecting the necks at the intersection point.

2. The instrument defined in claim 1, in which the body is elongated and the axis extends lengthwise of the body.

3. The instrument defined in claim 1, in which the axis passes between the necks.

4. The instrument defined in claim 1, in which the necks include substantially parallel distal portions disposed close together when the jaws are in the lens grasping position, and the necks further including substantially parallel proximate portions remote from the jaws which proximate portions are disposed close together when the jaws are in the lens releasing position, said proximate and distal portions meeting at the intersection point and being angled relative to each other.

5. The instrument defined in claim 1, including a step between the jaws and the necks, the jaws and necks extending generally parallel to each other but being offset by the step.

6. The instrument defined in claim 5, in which the jaws and necks are offset achieved by the step is about 1 millimeter.

7. The instrument defined in claim 1, including means for biasing the jaws and necks to the lens grasping position.

8. The instrument defined in claim 1, in which the necks are about 6.5 millimeters long.

9. The instrument defined in claim 1, in which each neck has one end adjacent to the jaws and a second, opposite end adjacent to the body, the intersection point being approximately mid-way between the first and second ends of each neck.

10. The instrument defined in claim 1, in which the intersection point is positioned to be located approximately 6 millimeters to 6.5 millimeters from the center of a lens grasped in the jaws.

11. The instrument defined in claim 1, in which the jaws are swingable relative to each other through an angle, and the body including means for limiting the angle of swinging of the jaws relative to each other.

12. An instrument for implanting an intraocular lens into a lens capsule, through a corneal slit of an eye, comprising two side-by-side jaws adapted to grasp the lens, two elongated necks joined, respectively, to the jaws and extending proximally therefrom in unconnected and uncrossed side-by-side relationship, and a body having two side portions swingable relative to each other, the side portions supporting the necks for swinging about an axis intersecting the necks at an intersection point adapted to be located at the corneal incision when the lens is held in the capsule by the jaws.

* * * * *

UNITED STATES PATENT AND TRADEMARK OFFICE
CERTIFICATE OF CORRECTION

PATENT NO. : 5,693,057
DATED : December 2, 1997
INVENTOR(S) : V. Dusek

It is certified that error appears in the above-indentified patent and that said Letters Patent is hereby corrected as shown below:

COLUMN     LINE 6       17     Delete "achieved"
(Claim 6,   line 2)

6       17     "step is" should read --step by--
(Claim 6,   line 2)

Signed and Sealed this

Twenty-eighth Day of April, 1998

Attest:

BRUCE LEHMAN

Attesting Officer      *Commissioner of Patents and Trademarks*

UNITED STATES PATENT AND TRADEMARK OFFICE
CERTIFICATE OF CORRECTION

PATENT NO. : 5,693,057
DATED : December 2, 1997
INVENTOR(S) : V. Dusek

It is certified that error appears in the above-identified patent and that said Letters Patent is hereby corrected as shown below:

Column 5, line 36, claim 1, line 5, "uncorrected" should read -- connected--

Signed and Sealed this

Nineteenth Day of May, 1998

Attest:

Attesting Officer

BRUCE LEHMAN

Commissioner of Patents and Trademarks